United States Patent [19]

Nedelec et al.

[11] 4,259,337
[45] Mar. 31, 1981

[54] METHOD FOR USING M-TRIFLUOROMETHYLPHENYL-PIPERIDINES

[75] Inventors: Lucien Nedelec, Le Raincy; Jacques Guillaume, Aulnay-sous-Bois; Claude Dumont, Nogent-sur-Marne, all of France

[73] Assignee: Roussel Uclaf, Paris, France

[21] Appl. No.: 796,317

[22] Filed: May 12, 1977

Related U.S. Application Data

[63] Continuation-in-part of Ser. No. 768,484, Feb. 14, 1977, abandoned.

[30] Foreign Application Priority Data

Feb. 13, 1976 [FR] France .................. 76 03933

[51] Int. Cl.³ .................. A61K 31/445; C07D 211/18
[52] U.S. Cl. .................. 424/267; 546/192; 546/222; 546/216; 546/346; 546/226; 546/227
[58] Field of Search .................. 260/293.72; 424/267; 546/192

[56] References Cited

U.S. PATENT DOCUMENTS 2,891,066   6/1959   Parcell .................. 260/293.72

OTHER PUBLICATIONS

Yale, "Journal of Medicinal and Pharmaceutical Chemistry," vol. 1, No. 2, (1959), pp. 121-133.
Burger, Medicinal Chemistry, Third Ed., Wiley-Interscience Publishers, Inc., New York, pp. 1433-1477, (1970).

McElvain et al., "J. Am. Chem. Soc.," vol. 55, pp. 4625-4629, (1933).
Julia et al., "Bull. Soc. Chim. France," (1968), No. 3, pp. 987-1012.
Iselin et al., "Helv. Chimica Acta," vol. 37, pp. 178-184, (1954).
Fuller et al., "Arch. Int. Pharmacodyn.," vol. 214, pp. 263-270, (1975).

Primary Examiner—Robert T. Bond
Attorney, Agent, or Firm—Hammond & Littell, Weissenberger and Muserlian

[57] ABSTRACT

Novel m-trifluoromethylphenyl-piperidines of the formula

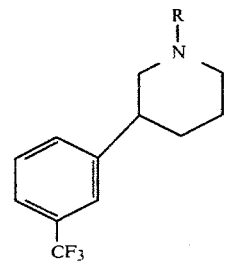

wherein R is selected from the group consisting of hydrogen, branched or straight chain alkyl of 1 to 5 carbon atoms, alkenyl of 3 to 5 carbon atoms, alkynyl of 3 to 5 carbon atoms and phenyl alkyl of 1 to 3 alkyl carbon atoms and their non-toxic, pharmaceutically acceptable acid addition salts having antidepressive, anorexigenic and antiparkinsonian activity and their preparation and novel intermediates formed therein.

4 Claims, No Drawings

METHOD FOR USING M-TRIFLUOROMETHYLPHENYL-PIPERIDINES

PRIOR APPLICATION

This application is a continuation-in-part application of our copending, commonly assigned U.S. patent application Ser. No. 768,484 filed Feb. 14, 1977, now abandoned.

OBJECTS OF THE INVENTION

It is an object of the invention to provide the novel m-trifluoromethylphenyl-piperidines of formula I and their non-toxic, pharmaceutically acceptable acid addition salts.

It is another object of the invention to provide a novel process and novel intermediates for the preparation of the compounds of formula I.

It is a further object of the invention to provide novel compositions for treating depression, treating obesity and for treating symptoms of Parkinson disease.

It is an additional object of the invention to provide a novel method of relieving depression, curbing the appetite and treating the symptoms of Parkinson disease in warm-blooded animals.

These and other objects and advantages of the invention will become obvious from the following detailed description.

THE INVENTION

The novel products of the invention are selected from the group consisting of m-trifluoromethylphenyl-piperidines of the formula

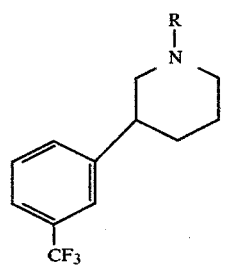

I wherein R is selected from the group consisting of hydrogen, branched or straight chain alkyl of 1 to 5 carbon atoms, alkenyl of 3 to 5 carbon atoms, alkynyl of 3 to 5 carbon atoms and phenyl alkyl of 1 to 3 alkyl carbon atoms and their non-toxic, pharmaceutically acceptable acid addition salts.

In the compounds of formula I, examples of R are alkyl such as methyl, ethyl, propyl, isopropyl, butyl, isobutyl and pentyl; alkenyl such as allyl; alkynyl such as propargyl; and phenylalkyl such as benzyl, phenethyl and phenyl-2-propyl.

Examples of suitable acids for the formation of the acid addition salts are inorganic acids such as hydrochloric acid, hydrobromic acid, hydroiodic acid, nitric acid, sulfuric acid or phosphoric acid and organic carboxylic acids such as acetic acid, formic acid, benzoic acid, maleic acid, fumaric acid, succinic acid, tartaric acid, citric acid, oxalic acid, glyoxylic acid or aspartic acid and alkane sulfonic acids such as methane sulfonic acid and aryl sulfonic acids such as benzene sulfonic acid.

A preferred group of compounds of formula I are those where R is hydrogen, methyl, ethyl, propyl, isopropyl, benzyl and phenethyl and their acid addition salts. Particularly preferred are the compounds of formula I wherein R is hydrogen, methyl, propyl, isopropyl or benzyl and their acid addition salts. Specific preferred compounds of formula I are 3-(m-trifluoromethylphenyl)-piperidine; N-methyl-3-(m-trifluoromethylphenyl)-piperidine, N-isopropyl-3-(m-trifluoromethylphenyl)-piperidine, N-propyl-3-(m-trifluoromethylphenyl)-piperidine and N-benzyl-3-(m-trifluoromethylphenyl)-piperidine and their non-toxic, pharmaceutically acceptable acid addition salts.

The novel process of the invention for the preparation of a compound of formula I comprises reacting m-trifluoromethylphenyl bromide with magnesium in anhydrous ether to obtain m-trifluoromethylphenyl magnesium bromide, reacting the latter with N-benzyl-piperid-3-one to obtain a compound of the formula

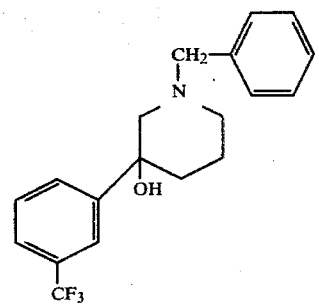

II reacting the latter with an acetylating agent to obtain a compound of the formula

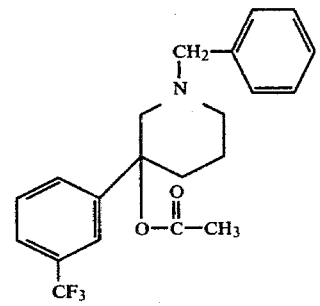

III acidifying the latter with hydrochloric acid to obtain the corresponding hydrochloride and subjecting the latter to hydrogenolysis to obtain the hydrochloride salt of a compound of the formula

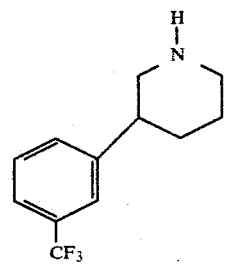

Ia and either isolating the product or alkalize the latter to obtain the free base which may be salified if desired or reacting the compound of formula Ia in the form of its free base with a halide of the formula R'-Hal      IV wherein Hal is chlorine, bromine or iodine and R' is selected from the group consisting of alkyl of 1 to 5 carbon atoms, alkenyl and alkynyl of 3 to 5 carbon atoms and phenylalkyl of 1 to 3 alkyl carbon atoms to obtain a compound of the formula

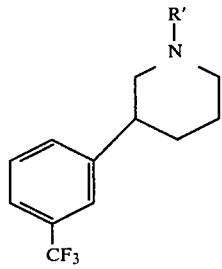

Ib which may be isolated and salified, if desired.

A preferred mode of the process of the invention includes reacting m-trifluoromethylphenyl bromide with magnesium in an anhydrous ether such as tetrahydrofuran or ethyl ether and the reaction of the corresponding magnesium halide compound with N-benzyl-piperid-3-one is also effected in an anhydrous organic solvent such as tetrahydrofuran and ethyl ether. The acetylation of the compound of formula II is effected with heating with acetic acid anhydride in the presence of sulfuric acid and the hydrogenolysis is effected with hydrogen in the presence of a catalyst such as palladium in a low molecular weight alkanol such as methanol or ethanol. The reaction with halide or formula IV is effected in an organic solvent such as acetone in the presence of silver oxide or sodium carbonate.

In a variation of the process for the preparation of a compound of formula Ia, the product of formula II is deshydrated to obtain a compound of the formula

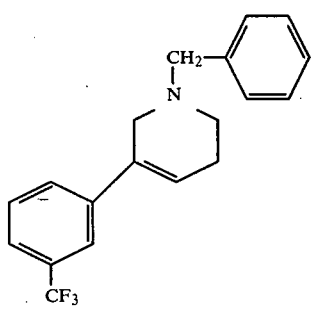

V which is then hydrogenated to obtain compound of formula Ia which may be isolated or salified, if desired.

In a preferred mode of this variation, the deshydration is effected at reflux with an energetic deshydration agent such as polyphosphoric acid, phosphoric acid anhydride or p-toluene sulfonic acid, in an organic solvent such as xylene. The hydrogenation is effected with gaseous hydrogen in the presence of a catalyst such as palladium, for example, in acetic acid.

In another variation of the process for the preparation of a compound of formula I wherein R is straight chain alkyl of 1 to 5 carbon atoms, a compound of formula $I_A$ is reacted either with an acid anhydride of the formula

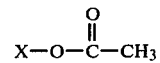

wherein X is formyl to obtain a compound of the formula

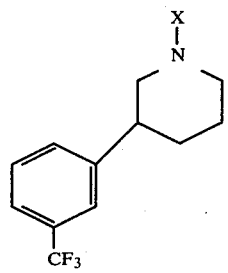

VI wherein X is formyl or with an acid anhydride of the formula Y-O-Y wherein Y is acyl of an alkanoic acid of 2 to 5 carbon atoms or with an acid chloride of formula Y-Cl wherein Y has the above definition to obtain a compound of the formula

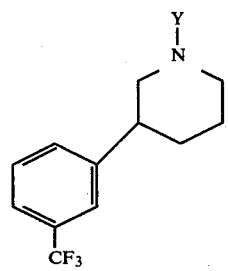

VII and reducing the compound of formula VI or VII to obtain the corresponding compound of formula I wherein R is straight chain alkyl of 1 to 5 carbon atomss which may be salified, if desired.

The preferred reaction conditions of this process variation comprises effecting the first step in an organic solvent such as benzene and the second reducing step is effected with lithium aluminum hydride in an organic solvent such as tetrahydrofuran.

The compounds of formula I are basic and the acid addition salts thereof may be prepared by reacting the base with an organic or inorganic acid in approximately stoichiometric amounts in a known manner.

The novel compositions of the invention having antidepressive, antiparkinsonian and anorexigenic activity are comprised of an effective amount of at least one compound of formula I and their acid addition salts and an inert pharmaceutical carrier or excipient. The compositions may be in the form of tablets, dragees, gelules, granules, suppositories or injectable solutions or suspensions.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, preservatives, diverse wetting agents, emulsifiers or dispersants.

The compositions are useful for the treatment of depression, melancholy, manic-depressive psychosis, reactional and exhausted depressions, neurotic depressions, obesity and symptons of Parkinson disease.

A preferred group of compositions of the invention contain compounds of formula I where R is hydrogen, methyl, ethyl, propyl, isopropyl, benzyl or phenethyl and their acid addition salts. Particularly preferred are the compositions of compounds of formula I wherein R is hydrogen, methyl, propyl, isopropyl or benzyl and their acid addition salts. Specific preferred compositions contain 3-(m-trifluoromethylphenyl)-piperidine, N-methyl-3-(m-trifluoromethylphenyl)-piperidine, N-isopropyl-3-(m-trifluoromethylphenyl)-piperidine, N-propyl-3-(m-trifluoromethylphenyl)-piperidine and N-benzyl-3-(m-trifluoromethylphenyl)-piperidine and their non-toxic, pharmaceutically acceptable acid addition salts.

The novel method of the invention for relieving depression, curbing the appetite and treating the symptoms of Parkinson disease in warm-blooded animals, including humans, comprises administering to warm-blooded animals an effective amount of at least one compound of formula I and its non-toxic, pharmaceutically acceptable acid addition salts. The compounds may be administered orally, rectally or parenterally and the usual daily dose is depending upon the method of administration and the specific product.

The usual daily dose is, for example, 0.2 to 6 mg/kg by oral rout in human.

The novel intermediates of the invention have the formulae

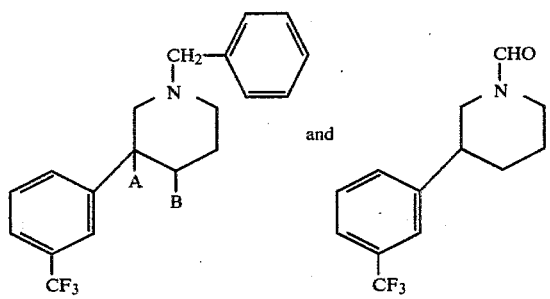

wherein A is -OH or acetoxy and B is hydrogen or A and B together form a double bond.

In the following examples there are described several preferred embodiments to illustrate the invention. However, it should be understood that the invention is not intended to be limited to the specific embodiments.

EXAMPLE 1

3-(m-trifluoromethylphenyl)-piperidine hydrochloride

STEP A:
N-benzyl-3-hydroxy-3-(m-trifluoromethylphenyl)-piperidine

A crystal of iodine was added to a suspension of 11 g of magnesium in 15 ml of ether and a solution of 100 mg of 3-trifluoromethylphenyl bromide in 300 ml of ether was added thereto over 105 minutes. The mixture was stirred for 2 hours at room temperature to obtain a solution of 3-trifluoromethylphenyl magnesium bromide and a solution of 70 g of N-benzyl-piperid-3-one in 300 ml of ether was added thereto at 5° C. over an hour. The mixture was stirred on an icewater bath for 15 minutes and then for an hour at room temperature. The reaction mixture was then slowly added to 800 ml of water-ice mixture for hydrolysis and the mixture was stirred and filtered. The filtrate was extracted 4 times with 400 ml of 2 N hydrochloric acid and once with aqueous sodium chloride solution. The acid solution was cooled on an ice bath and was made alkaline with triethylamine. The mixture was extracted with ethyl acetate and the organic phase was washed with aqueous sodium chloride solution, was dried over magnesium sulfate and evaporated to dryness to obtain 100 mg of raw product. The latter was chromatographed over silica gel and was eluted with a 85-10-5 cyclohexane-chloroform-triethylamine mixture to obtain after evaporation 72 g of N-benzyl-3-hydroxy-3-(m-trifluoromethylphenyl)-piperidine in the form of an orange resin.

| U.V. Spectrum (ethanol): | | |
|---|---|---|
| inflex. towards 253 nm | $E_1{}_{cm}{}^{1\%} = 21$ | |
| max. at 259 nm | $E_1{}_{cm}{}^{1\%} = 24$ | $\epsilon = 800$ |
| max. at 263 nm | $E_1{}_{cm}{}^{1\%} = 26$ | $\epsilon = 870$ |
| max. at 270 nm | $E_1{}_{cm}{}^{1\%} = 21$ | $\epsilon = 700$ |

STEP B: acetate of
N-benzyl-3-(m-trifluoromethylphenyl)-piperidin-3-ol-hydrochloride 0.3 ml of concentrated sulfuric acid was added to a mixture of 37 g of the product of Step A in 220 ml of acetic acid anhydride and the mixture was heated at 110° C. for an hour. After cooling, the mixture was poured into ice water and was stirred for 15 minutes. The mixture was alkalinized with sodium hydroxide solution and was then extracted with ethyl acetate. The organic phase was added with aqueous sodium chloride solution, was dried over magnesium sulfate and evaporated to dryness to obtain 39 g of the acetate of N-benzyl-3-(m-trifluoromethylphenyl)-piperid-3-one in the form of a resin.

The said 39 g of product were dissolved in 600 ml of ethyl acetate and while cooling the solution on an ice bath, 100 ml of ethanol saturated with hydrochloric acid were added thereto. The mixture was evaporated to dryness under reduced pressure and the resin was added to 200 ml of ethyl acetate. 200 ml of ether were then added to the mixture to effect crystallization and the mixture was filtered. The product was rinsed with ether and dried to obtain 36 g of the acetate of N-benzyl-3-(m-trifluoromethylphenyl)-piperidin-3-ol hydrochloride in the form of colorless crystals melting at 206°–207° C.

STEP C: 3-(m-trifluoromethylphenyl)-piperidine hydrochloride 40 g of 10% palladized carbon were added to a mixture of 36 g of the product of Step B in 700 ml of ethanol and hydrogen was absorbed until saturation was reached. The mixture was filtered and the filtrate was evaporated to dryness under reduced pressure. The crystals were washed with ether and dried to obtain 21 g of 3-(m-trifluoromethylphenyl)-piperidine hydrochloride in the form of colorless crystals melting at 200° C.

EXAMPLE 2

3-(m-trifluoromethylphenyl)-piperidine hydrochloride

STEP A:
N-benzyl-3-(m-trifluoromethylphenyl)-1,2,5,6-tetrahydropyridine 20 g of phosphoric acid anhydride was added to a solution of 20 g of N-benzyl-3-hydroxy-3-(m-trifluoromethylphenyl)-piperidine in 200 ml of xylene and the mixture was refluxed for 75 minutes. After cooling the mixture was poured into 200 ml of ice water and the mixture was neutralized by slow addition of triethylamine. The aqueous phase was extracted with methylene chloride and the organic phase was washed with aqueous sodium chloride solution, dried over magnesium sulfate and evaporated to dryness to obtain 22 g of raw product. The latter was purified by chromatography over silica gel and elution with a 90-5-5 cyclohexane-chloroform-triethylamine mixture to obtain 11 g of N-benzyl-3-(trifluoromethylphenyl)-1,2,5,6-tetrahydropyridine.

| U.V. Spectrum (ethanol): | | |
| --- | --- | --- |
| max. at 246 nm | $E_{1\,cm}^{1\%} = 280$ | $\epsilon = 8,900$ |
| max. at 317 nm | $E_{1\,cm}^{1\%} = 38$ | $\epsilon = 1,200$ |

STEP B: 3-(m-trifluoromethylphenyl)-piperidine hydrochloride

A solution of 2.95 g of the product of Step A in 15 ml of acetic acid was added to a suspension of 3.5 g of 10% palladized carbon in 15 ml of acetic acid and hydrogen was absorbed until saturation (600 ml of $H_2$). The mixture was filtered and the filtrate was evaporated to dryness under reduced pressure to obtain 3 g of raw product. The latter was dissolved in 50 ml of water and the solution was neutralized with sodium carbonate. The mixture was extracted with methylene chloride and the extracts were washed with aqueous sodium chloride solution, dried over magnesium sulfate and evaporated to dryness to obtain 1.8 g of 3-(m-trifluoromethylphenyl)-piperidine in the form of a yellow oil.

The said product was dissolved in 10 ml of ethyl acetate and 25 ml of a solution of hydrochloric acid in ethyl acetate were added thereto. After crystallization, the mixture was filtered and the solid product was washed with ethyl acetate and dried under reduced pressure to obtain 1.65 g of hydrochloride salt. The latter was crystallized from acetonitrile to obtain 1.45 g of 3-(m-trifluoromethylphenyl)-piperidine hydrochloride in the form of colorless crystals identical to the product of Example 1.

Analysis: $C_{12}H_{14}F_3N.HCl$; molecular weight=264.714; Calculated: %C 54.24, %H 5.69, %Cl 13.34, %F 21.45, %N 5.27; Found: 54.2, 5.7, 13.3, 21.4, 5.0.

EXAMPLE 3

N-methyl-3-(m-trifluoromethylphenyl)-piperidine hydrochloride

STEP A:
3-(m-trifluoromethylphenyl)-1-piperidine-carboxaldehyde 3.8 g of mixed formic acid-acetic acid anhydride were added to a solution of 9.8 g of 3-(m-trifluoromethylphenyl)-piperidine in 100 ml of anhydrous benzene and the mixture was stirred for 15 minutes at room temperature and was then poured into 100 ml of aqueous sodium bicarbonate. The mixture was extracted with ethyl acetate and the organic extracts were washed with aqueous sodium chloride, dried over magnesium sulfate and evaporated to dryness to obtain 10 g of 3-(m-trifluoromethylphenyl)-1-piperidine-carboxaldehyde in the form of a colorless resin which was used as is for the next step.

STEP B:
N-methyl-3-(m-trifluoromethylphenyl)-piperidine hydrochloride 2 g of lithium aluminum hydride were added in small amounts to 100 ml of tetrahydrofuran and the mixture was cooled to 7° C. A solution of 10 g of the product of Step A in 60 ml of tetrahydrofuran was added thereto over about 20 minutes while keeping the temperature at 5° to 10° C. and the mixture was stirred for an hour at room temperature and was then poured into ice. The mixture was stirred for 15 minutes at room temperature and was then filtered. The filtrate was extracted with ethyl acetate and the organic phase was washed with aqueous sodium chloride solution, dried over magnesium sulfate and evaporated to dryness to obtain 9.1 g of N-methyl-3-(m-trifluoromethylphenyl)-piperidine in the form of a resin.

The said product was dissolved in 200 ml of ethyl acetate and 40 ml of ethyl acetate saturated with hydrochloric acid were added thereto. The solution was concentrated and placed in a refrigerator for crystallization. The mixture was filtered and the solid product was washed with ethyl acetate, then with ether to obtain 6.2 g of impure hydrochloride salt melting at 185° C. 5.8 g of the said product were dissolved in 20 ml of methanol and then the solution was reduced in half by volume while replacing the methanol as it distilled with ethylacetate. The mixture crystallized and was filtered. The product was rinsed with ether to obtain 5.5 g of N-methyl-3-(m-trifluoromethylphenyl)-piperidine hydrochloride in the form of colorless crystals melting at 188° C.

Analysis: $C_{13}H_{16}F_3N.HCl$; molecular weight=279.741; Calculated: %C 55.82, %H 6.13, %N 5.01, %Cl 12.67, %F 20.38; Found: 55.7, 6.2, 4.9, 12.6, 20.4.

EXAMPLE 4

N-isopropyl-3-(m-trifluoromethylphenyl)-piperidine hydrochloride 3.4 g of silver oxide were added to a solution of 9.2 g of 3-(m-trifluoromethylphenyl)-piperidine in 45 ml of acetone and after 6½ hours of stirring 1.1 g of silver oxide and 4.9 ml of isopropyl iodide were added. The mixture was stirred for 24 hours and was filtered. The filtrate was evaporated to dryness to obtain 10.4 g of N-isopropyl-3-(m-trifluoromethylphenyl)-piperidine.

The latter product was dissolved in 150 ml of ether and the temperature was lowered to 5° C. 20 ml of ethyl acetate staturated with hydrogen chloride was added thereto while keeping the temperature below 10° C. and the mixture was stirred in an ice bath. 50 ml of ether were added thereto and the mixture mixture was filtered. The filtrate was evaporated to dryness to obtain 10.2 g of product. The latter was crystallized from acetonitrile to obtain 7.45 g of N-isopropyl-3-(m-trifluoromethylphenyl)-piperidine hydrochloride in the form of colorless crystals melting at 213° C.

Analysis: $C_{15}H_{20}F_3N.HCl$; molecular weight=307.803; Calculated: %C 58.5, %H 6.9, %Cl 11.5, %F 18.5, %N 4.55; Found: 58.4, 6.9, 11.8, 18.1, 4.4.

EXAMPLE 5

N-propyl-3-(m-trifluoromethylphenyl)-piperidine oxalate

STEP A: 3-(m-trifluoromethylphenyl)-piperidine 5 g of 3-(m-trifluoromethylphenyl)-piperidine hydrochloride were dissolved in water and the solution was cooled on an ice bath and was made alkaline with sodium hydroxide. The mixture was extracted with ether and the ether were washed with water, dried over magnesium sulfate and evaporated to dryness under reduced pressure to obtain 4.6 g of 3-(m-trifluoromethylphenyl)-piperidine.

STEP B: N-propyl-3-(m-trifluoromethylphenyl)-piperidine oxalate

A mixture of 4.6 g of the product of Step A in 25 ml of acetone was stirred until dissolution occured and then 2.5 g of silver oxide were added thereto. The mixture was cooled on an ice bath and 2.5 ml of propyl iodide were added dropwise over 5 minutes. The temperature went back to room temperature and the mixture was stirred for 16 hours and was filtered. The filtrate was evaporated to dryness under reduced pressure and the residue was chromatographed over silica gel. Elution with a 85-10-5 cyclohexane-chloroform-triethylamine mixture and evaporation to dryness under reduced pressure yielded 4.3 g of N-propyl-3-(m-trifluoromethylphenyl)-piperidine.

1.2 g of oxalic acid were added to a solution of 4.2 g of the said product in 21 ml of isopropyl and when the mixture became lukewarm, the product dissolved. The crystallization was started and the mixture was iced and vacuum filtered. The product was washed with isopropanol, vacuum filtered and crystallized from isopropanol to obtain 5.28 g of N-propyl-3-(m-trifluoromethylphenyl)-piperidine oxalate in the form of colorless crystals melting at 172°–173° C.

Analysis: $C_{17}H_{22}F_3NO_4$; molecular weight=361.374; Calculated: %C 56.50, %H 6.14, %F 15.77, %N 3.88; Found: 56.8, 6.2, 15.7, 3.8.

EXAMPLE 6

N-benzyl-3-(m-trifluoromethylphenyl)-piperidine hydrochloride 2.2 g of silver oxide were added to a mixture of 4.6 g of 3-(m-trifluoromethylphenyl)-piperidine and 22 ml of acetone and the mixture was cooled on an ice water bath while 2.55 ml (≃3.6 g) of benzyl bromide was added dropwise over 10 minutes at a temperature less than 10° C. The mixture was stirred at 0° C. for one hour and was filtered. The filtrate was evaporated to dryness under reduced presssure to obtain 7 g of raw product which was chromatographed over silica gel. Elution with an 85-10-5 cyclohexane-chloroformtriethylamine mixture and evaporation to dryness under reduced pressure yielded 4.99 g of N-benzyl-3-(m-trifluoromethylphenyl)-piperidine.

The said product was dissolved in 50 ml of ethyl acetate and a solution of ethyl acetate saturated with hydrogen chloride was added thereto to obtain an acid pH. The mixture was iced and vacuum filtered and the product was rinsed with ethyl acetate and was dried under reduced pressure to obtain 4.98 g of product which was crystallized from isopropanol. The product was dried to obtain 4.66 g of N-benzyl-3-(m-trifluoromethylphenyl)-piperidine hydrochloride in the form of colorless crystals melting at 245° C.

Analysis: $C_{19}H_{21}ClF_3N$; molecular weight=355.843; Calculated: %C 64.13, %H 5.95, %Cl 9.96, %F 16.02, %N 3.93; Found: 64.2, 6.0, 10.1, 16.1, 3.9.

EXAMPLE 7

Tablets were prepared containing 25 mg of N-methyl-3-(m-trifluoromethylphenyl)-piperidine hydrochloride or N-isopropyl-3-(m-trifluoromethylphenyl)-piperidine hydrochloride or N-propyl-3-(m-trifluoromethylphenyl)-piperidine oxalate or N-benzyl-3-(m-trifluoromethylphenyl)-piperidine hydrochloride and sufficient excipient of lactose, starch, talc and magnesium stearate for a final tablet weight of 150 mg.

PHARMACOLOGICAL DATA

(1) Potentiation of stereotypes provoked by dexamphetamine

The tests are carried out on groups of 5 male rats weighing about 150 to 180 g. Each animal was placed individually in a grilled cage (29×25 ×17 cm) containing a few wood shavings. A does of 3 mg/kg of dexamphetamine sulfate was injected intraperitoneally one half hour after the intraperitoneal administration of the product studied. The behavior of the animals was noted every half hour for 5 hours with the rating recommended by HALLIWELL et al [Brit. J. Pharmacol., Vol. 23 (1964), p. 330–350]. The animalis asleep (0), he is awake but immobile (1), he is turning in his cage (2), he is sniffing the lid (3), he is licking the sides (4), he is touching the shavings or the bars of the cage with his teeth (5), he is biting the chips or bars of the cage (6). The total of the scores per group at different periods after the administration of the product studied was determined and the potentiation of the stereotypies evaluated at the height of the effect is expressed by an increasing number of + signs for a given dose.

The results obtained appear in the Table below:

TABLE I

| Products of Example | Potentiation of stereotypies provoked by dexamphetamine for a determined dose in mg/kg | |
|---|---|---|
| 3 | ++ | 2 |
| 4 | +++ | 0.2 |
| 5 | +++ | 0.5 |
| 6 | ++ | 20 |

The results show, in particular, that the products of Examples 4 and 5 have a very high activity of potentiation of stereotypies provoked by dexamphetamine.

(2) Antagonism of catalepsy provoked by prochlorpemazine

The tests are carried out on groups of 5 young rats weighing about 100 g and the cataleptigenic agent used is prochlorpemazine at a dose of 15 mg/kg intraperitoneally. The product studied was administered simultaneously in the same way. The intensity of the catalepsy was evaluated by the test of crossing of the homolateral paws [BOISSIER et al, Therapie, Vol. 18 (1963), p. 1257] every hour for 7 hours. The rating adopted is the following: the animal refuses the crossing of the front paws with the homolateral rear paws (0), he retains the desired crossing on one side only (0.5), he accepts the crossing on both sides (1). The sum of the scores by groups read at different periods after the administration of the product studied is determined. The antagonism of catalepsy provoked by prochlorpemazine evaluated at the height of the effect was expressed by an increasing number of + signs for a given dose and the results are reported in Table II.

TABLE II

| Product of Example | Antagonism of catalepsy provoked by prochloropemazine for a determined dose in mg/kg | |
|---|---|---|
| 1 | ++ | 20 |
| 3 | + | 20 |
| 4 | +++ | 50 |

These results show in particular that the products in Examples 1 and 4 exert a substantial antagonism toward the cataleptigenic activity of prochlorpemazine.

(3) Antagonism with respect to reserpinic regidity

The antagonism of the compounds with respect to reserpinic rigidity [Jurna I: Arch. Pharmak. Exp. Path. Vol. 260 (1968), p. 80–88] was studied on the rat. The tests consisted of recording, by means of electrodes placed on the muscles of the anterior cavity of one of the rear paws of the animal, the electromyogram (E.M.G.) provoked by a dorsiflection of the instep. A dose of 10 mg/kg of reserpine was administered intraveneously, then, one half hour later when the hypertonicity of the muscle was maximal, the product to be studied was administered in the same way at a dose of 10 mg/kg or of 20 mg/kg.

The electromyographic responses obtained before and after treatment, were compared in intensity and in time. The inhibition observed on the electromyogram expressed the antagonism exercised by the product with respect to the rigidity provoked by reserpine. It was expressed by an increasing number of + signs for a given dose expressed in mg/kg. The results obtained appear in Table III.

TABLE III

| Product of Example | Antagonism to reserpinic rigidity for a determined dose in mg/kg | |
|---|---|---|
| 1 | ++ | 20 |
| 3 | ++ | 20 |
| 4 | ++ | 10 |

The results obtained show, in particular that the product of Example 4 has very high activity.

(4) Anorexigenic activity in mice

The anorexigenic activity was studied with mice and the animals receive the product studied intraperitoneally 30 minutes before the start of the test. The quantities of nourishment absorbed in the course of the following 24 hours was noted and compared with the quantity of nourishment absorbed in the course of the same period by animals not receiving the product studied. The anorexigenic activity was expressed by an increasing number of + signs for a given dose expressed in mg/kg. Under the conditions of the test, the anorexigenic activity of the products in Examples 1 and 4 was represented by one + sign, and that of the product in Example 5 by two ++ signs for a dose of 20 mg/kg.

(5) Anorexigenic activity in the dog

The anorexigenic activity was studied on the dog using the method of ADAMS et al [J. Pharm. Sci., Vol. 53 (1964), p. 1405]. On the day of the test of a substance presumed to be anorexigenic, the individual daily ration of the animals was broken down into substantially equal balls (10 to 20 g) which were offered to the dogs every 10 minutes for 7 hours. Normally, the animals regularly accept the successive balls offered to them. Refusal translates the anorexiant effectiveness of the compound studied which was administered in the first ball. The anorexigenic activity was expressed by an increasing number of + signs for a given dose expresses in mg/kg. Under the condition of the test, the anorexigenic activity of the product of Example 1 was represented by one + sign for a dose of 20 mg/kg, that of the product of Example 4 by one + sign for a dose of 25 mg/kg and that of the product of Example 5 by two + signs for a dose of 15 mg/kg.

(6) Acute toxicity

The $LD_{50}$, the dose at which 50% of the mice died after the intraperitoneal administration of the products to mice was determined 48 hours after the administration. The $LD_{50}$ for the products of Examples 1 and 6 was about 150 mg/kg, of Examples 3 and 4 was about 100 mg/kg and of Example 5 was about 160 mg/kg.

Various modifications of the products and process of the invention may be made without departing from the spirit or scope thereof and it is to be understood that the invention is to be limited only as defined in the appended claims.

We claim:

1. A method of relieving depression in warm-blooded animals comprising administering to warm-blooded animals an antidepressant effective amount of at least one compound selected from the group consisting of m-trifluoromethylphenyl-piperidine of the formula

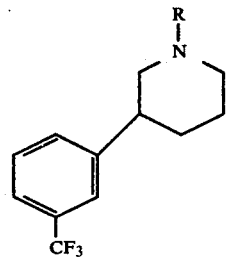

wherein R is selected from the group consisting of hydrogen, branched or straight chain alkyl of 1 to 5 carbon atoms, alkenyl of 3 to 5 carbon atoms and phenylalkyl of 1 to 3 alkyl carbon atoms and their non-toxic, pharmaceutically acceptable acid addition salts.

2. The method of claim 1 wherein R is selected from the group consisting of hydrogen, methyl, ethyl, propyl, isopropyl, benzyl and phenethyl.

3. The method of claim 1 wherein R is selected from the group consisting of hydrogen, methyl and isopropyl.

4. The method of claim 1 wherein the compound is selected from the group consisting of 3-(m-trifluoromethylphenyl)-piperidine hydrochloride, N-methyl-3-(m-trifluoromethylphenyl)-piperidine hydrochloride, N-isopropyl-3-(m-trifluoromethylphenyl)-piperidine hydrochloride, N-benzyl-3-(m-trifluoromethylphenyl)-piperidine hydrochloride and N-propyl-3-(m-trifluoromethylphenyl)-piperidine oxalate.

* * * * *